United States Patent

Behler et al.

[11] Patent Number: 5,565,598
[45] Date of Patent: Oct. 15, 1996

[54] PROCESS FOR THE PRODUCTION OF SUBSTANTIALLY ODORLESS FATTY ALCOHOL ETHERSULFATE SALTS

[75] Inventors: Ansgar Behler, Bottropp; Uwe Ploog, Haan; Michael Koehler, Mettmann; Hermann Hensen, Haan; Werner Seipel, Hilden; Guenther Demmering, Solingen; Horst-Dieter Komp, Langenfeld, all of Germany

[73] Assignee: Henkel Kommanditgesellschaft auf Aktien, Duesseldorf, Germany

[21] Appl. No.: 347,332

[22] PCT Filed: May 24, 1993

[86] PCT No.: PCT/EP93/01300

§ 371 Date: Nov. 30, 1994

§ 102(e) Date: Nov. 30, 1994

[87] PCT Pub. No.: WO93/24453

PCT Pub. Date: Dec. 9, 1993

[30] Foreign Application Priority Data

Jun. 1, 1992 [DE] Germany .......................... 42 18 075.9

[51] Int. Cl.$^6$ .................................................. C07C 305/10
[52] U.S. Cl. ................................................ 558/34; 558/31
[58] Field of Search ........................................ 558/34, 31

[56] References Cited

U.S. PATENT DOCUMENTS

| | | | |
|---|---|---|---|
| 4,645,627 | 2/1987 | Van Paassen et al. | 558/34 |
| 4,885,379 | 12/1989 | Abend | 558/34 |

FOREIGN PATENT DOCUMENTS

| | | |
|---|---|---|
| 195617 | 5/1982 | Czechoslovakia . |
| 0337406 | 10/1989 | European Pat. Off. . |
| 0401642 | 12/1990 | European Pat. Off. . |
| 3933860 | 4/1991 | Germany . |
| 49-053610 | 5/1974 | Japan . |
| 62-265258 | 11/1987 | Japan . |
| 63-039993 | 2/1988 | Japan . |
| 63-039994 | 2/1988 | Japan . |
| 2-004762 | 6/1990 | Japan . |

*Primary Examiner*—Nicky Chan
*Attorney, Agent, or Firm*—Ernest G. Szoke; Wayne C. Jaeschke; Henry E. Millson, Jr.

[57] ABSTRACT

A process for the production of a mixture of substantially odorless fatty alcohol ethersulfate salts corresponding to formula (I):

$$R^1-(OCH_2CH_2)_n-O-SO_3X \qquad (I)$$

in which
- $R^1$ is an alkyl radical containing from 6 to 18 carbon atoms,
- n is a number of from 1 to 10, and
- X is an alkali metal, alkaline earth metal, ammonium, or alkanolammonium ion, comprising the steps of
- A) ethoxylating a fatty alcohol mixture in which the content of components having a boiling point below 235° C. is not more than 0.5% by weight, based on the weight of the fatty alcohol mixture;
- B) sulfating the fatty alcohol ethoxylate mixture from step A; and
- C) neutralizing the sulfated fatty alcohol ethoxylate mixture from step B to form said mixture of substantially odorless fatty alcohol ethersulfate salts.

12 Claims, No Drawings

PROCESS FOR THE PRODUCTION OF SUBSTANTIALLY ODORLESS FATTY ALCOHOL ETHERSULFATE SALTS

This application is a 371 of PCT/EP93/01300 filed May 24, 1993.

FIELD OF THE INVENTION

This invention relates to a process for the production of substantially odorless fatty alcohol ethersulfate salts in which selected fatty alcohol cuts are ethoxylated, sulfated and then neutralized.

PRIOR ART

Anionic surfactants of the fatty alcohol ethersulfate type are distinguished by high foaming power, high cleaning power and low sensitivity to hardness and fats. Since, in addition, they are safe from the ecotoxicological point of view, they are often used in the production of manual dishwashing detergents and cosmetic products, such as for example hair shampoos, foam or shower baths. A certain disadvantage attending the use of fatty alcohol ethersulfates lies in their fatty odor which generally necessitates perfuming. However, changing market requirements have recently resulted in an increasing demand for lightly perfumed or perfume-free products and hence for odor-improved starting materials.

Accordingly, the problem addressed by the present invention was to provide a process for the production of substantially odorless ethersulfates.

DESCRIPTION OF THE INVENTION

This invention relates to a process for the production of substantially odorless fatty alcohol ethersulfate salts corresponding to formula (I):

$$R^1-(OCH_2CH_2)_n-O-SO_3X \qquad (I)$$

in which $R^1$ is an alkyl radical containing 6 to 18 carbon atoms, n is a number of 1 to 10 and X is an alkali metal, alkaline earth metal, ammonium or alkanolammonium ion, by ethoxylation of fatty alcohols, sulfation of the resulting fatty alcohol ethoxylates and subsequent neutralization of the acidic sulfonation products, characterized in that technical fatty alcohol cuts are used in which the percentage content of volatile compounds, which have a boiling point under normal conditions below 235° C., is at most 0.5% by weight, based on the cut as a whole.

It has surprisingly been found that, after ethoxylation and sulfation, fatty alcohol cuts which meet this requirement give fatty alcohol ethersulfates which are substantially odorless and which completely satisfy market requirements. As the outcome of extensive analytical investigations, the invention includes the observation that all the odor-causing secondary constituents of technical fatty alcohols, such as for example short-chain aldehydes, ketones, etc., have a boiling point under normal conditions below 235° C.

In the context of the invention, normal conditions are understood to mean a temperature of 20° C. and an external pressure of 1 atm.

Fatty alcohol ethersulfates are known surfactants which are obtained in known manner by reaction of fatty alcohols with ethylene oxide and subsequent sulfation of the resulting fatty alcohol ethoxylates. The process has proved to be of particular advantage for the production of substantially odorless fatty alcohol ether sulfates corresponding to formula (I), in which $R^1$ is an alkyl radical containing 12 to 14 carbon atoms, n is a number of 2 to 5 and X represents sodium, magnesium, ammonium and/or alkanolammonium.

The ethoxylation reaction may be carried out in the presence of basic catalysts, such as sodium methylate for example, or layer compounds, such as hydrophobicized hydrotalcite for example, at temperatures of 150° to 190° C. Depending on the catalyst used, the resulting fatty alcohol ethoxylates may have a conventional homolog distribution or even a narrow homolog distribution.

The sulfation of the fatty alcohol ethoxylates may be carried out with gaseous sulfur trioxide or, preferably, chlorosulfonic acid, the molar ratio of fatty alcohol ethoxylate to sulfonating agent being from 1:0.9 to 1:1.3 and preferably from 1:0.95 to 1:1.05. To minimize the dioxane content of the sulfation products, it has proved to be of advantage to carry out the reaction at temperatures in the range from 15° to 50° C. and preferably at temperatures in the range from 25° to 35° C. and to keep the time elapsing between sulfation and neutralization as short as possible. The neutralization of the acidic products may be carried out with aqueous bases, for example sodium hydroxide, potassium hydroxide, magnesium hydroxide, ammonia or triethanolamine.

Technical fatty alcohol cuts having the following composition may be used with advantage in the process according to the invention:

=<$C_{10}$=0.1 to 0.5% by weight $C_{12}$=20.0 to 80.0% by weight, preferably 25.0 to 75.0% by weight, and more particularly 50 to 75% by weight $C_{14}$=20.0 to 80.0% by weight, preferably 25.0 to 75.0% by weight, and more particularly 25 to 35% by weight >=$C_{16}$=0.5 to 1.0.

Fatty alcohol cuts of this type may be obtained, for example, by subjecting technical coconut oil fatty alcohol or palm kernel oil fatty alcohol with a C chain length of $C_8$ to $C_{18}$ to fractional distillation or rectification in known manner. To obtain a clear boiling limit which reliably guarantees the separation of components with a boiling point below 235° C., standard technical measures for improving separation efficiency may be adopted. These include in particular the use of packed columns, the choice of a high reflux ratio and, optionally, the use of stripping steam to remove high-boiling fractions.

COMMERCIAL APPLICATIONS

The fatty alcohol ethersulfate salts obtainable by the process according to the invention are substantially odorless. They are suitable, for example, for the production of lightly perfumed or perfume-free manual dishwashing detergents and cosmetic products, such as hair shampoos, foam or shower baths, in which they may be present in quantities of 1 to 50% by weight and preferably 5 to 35% by weight, based on the particular product.

The following Examples are intended to illustrate the invention without limiting it in any way.

EXAMPLES

Example 1 a) Ethoxylation. 835.1 g (4.3 moles) of a technical coconut oil fatty alcohol distillate having the following C chain composition:

C$_{10}$: 0.3% by weight
C$_{12}$: 71.8% by weight
C$_{14}$: 26.6% by weight
C$_{16}$: 0.9% by weight and 5.9 g of sodium methylate in the form of a 30% by weight solution in methanol were introduced into a 1.5 liter steel autoclave. The autoclave was purged with nitrogen and evacuated for 30 minutes at 100° C. 350 g (8 moles) of ethylene oxide were then introduced in portions under pressure at a temperature of 180° C., a pressure of 5 bar being established. After the ethylene oxide had been added, the mixture was left to react for 30 minutes. 1183 g of fatty alcohol ethoxylate (hydroxyl value: 205) were obtained.

b) Sulfation. 276 g (1 mole) of the fatty alcohol ethoxylate of Example 1a) were introduced into a four-necked flask equipped with a stirrer, thermometer, dropping funnel and waste gas outlet. 122.4 g (1.05 moles) of chlorosulfonic acid were added dropwise with stirring at such a rate that the reaction temperature did not exceed 35° C. On completion of the reaction, the HCl gas formed was removed by evacuation and the crude product was neutralized with aqueous 25% by weight sodium hydroxide solution. The composition of the product is shown in Table 1.

Comparison Example C1 a) Ethoxylation. Example 1a) was repeated using technical C$_{12/14}$ coconut oil fatty alcohol (Lorol® S, a product of Henkel KGaA, Düsseldorf, FRG) with the following C chain composition:

C$_{10}$: 2.0% by weight
C$_{12}$: 70.0% by weight
C$_{14}$: 27.0% by weight
C$_{16}$: 1.0% by weight The hydroxyl value of the product was 205.

b) Sulfation. 276 g of the fatty alcohol ethoxylate of Example 2a) were reacted with chlorosulfonic acid and neutralized in the same way as in Example 1b). The composition of the product is shown in Table 1.

TABLE

| | Composition of the products Percentages as % by weight | | | | | |
|---|---|---|---|---|---|---|
| Ex. | WAS % | US % | Na$_2$SO$_4$ % | NaCl % | H$_2$O % | Odor |
| 1 | 26.9 | 0.6 | 0.9 | 0.10 | 70.7 | Odor-free |
| C1 | 25.6 | 1.3 | 1.0 | 0.04 | 71.3 | Fatty |

Legend:
WAS = Washing-active substance (anionic surfactant content)
US = Unsulfonated substance

We claim:

1. A process for the production of a mixture of substantially odorless fatty alcohol ethersulfate salts corresponding to formula (I):

$$R^1—(OCH_2CH_2)_n—O—SO_3X \qquad (I)$$

in which
R$^1$ is an alkyl radical containing from 6 to 18 carbon atoms, n is a number of from 1 to 10, and
X is an alkali metal, alkaline earth metal, ammonium, or alkanolammonium ion,
comprising the steps of
A) preparing a fatty alcohol mixture in which the content of components having a boiling point below 235° C. is not more than 0,5% by weight, based on the weight of the fatty alcohol mixture, from a fatty alcohol mixture having a content of such components greater than 0.5% by weight by fractional distillation or rectification;
B) ethoxylating the fatty alcohol mixture from step A);
C) sulfating the fatty alcohol ethoxylate mixture from step B; and
D) neutralizing the sulfated fatty alcohol ethoxylate mixture from step C) to form said mixture of substantially odorless fatty alcohol ethersulfate salts.

2. The process of claim 1 wherein in step B) the fatty alcohol mixture has the following composition:
≦C$_{10}$ is present in from 0.1 to 0.5% by weight,
C$_{12}$ is present in from 20 to 80% by weight,
C$_{14}$ is present in from 20 to 80% by weight, and
≧C$_{16}$ is present in from 0.5 to 1.0% by weight.

3. The process of claim 2 wherein the C$_{12}$ component is present in from 25 to 75% by weight, and the C$_{14}$ component is present in from 25 to 75% by weight.

4. The process of claim 3 wherein the C$_{12}$ component is present in from 50 to 75% by weight, and the C$_{14}$ component is present in from 25 to 35% by weight.

5. The process of claim 3 wherein in the sulfate salts of formula I n is a number of from 2 to 5.

6. The process of claim 1 wherein step B) is carried out at a temperature in the range of from 150° to 190° C. and in the presence of a basic catalyst.

7. The process of claim 1 wherein step C) is carried out at a temperature in the range of from 15° to 50° C.

8. The process of claim 1 wherein step C) is carried out with chlorosulfonic acid or gaseous sulfur trioxide and the molar ratio of fatty alcohol ethoxylate to sulfating agent is from 1:0.9 to 1:1.3.

9. The process of claim 1 wherein step D) is carried out with sodium hydroxide, potassium hydroxide, magnesium hydroxide, ammonia, or triethanolamine.

10. The process of claim 1 wherein in step B) the fatty alcohol mixture has the following composition:
≦C$_{10}$ is present in from 0.1 to 0.5% by weight,
C$_{12}$ is present in from 25 to 75% by weight,
C$_{14}$ is present in from 25 to 75% by weight, and
≧C$_{16}$ is present in from 0.5 to 1.0% by weight;
step B) is carried out at a temperature in the range of from 150° to 190° C. and in the presence of a basic catalyst; and
step C) is carried out at a temperature in the range of from 15° to 50° C.

11. The process of claim 10 wherein the C$_{12}$ component is present in from 50 to 75% by weight, and the C$_{14}$ component is present in from 25 to 35% by weight.

12. The process of claim 1 wherein the fatty oil mixture subjected to fractional distillation or rectification is technical coconut oil fatty alcohol or technical palm kernel oil fatty alcohol.

* * * * *